(12) United States Patent
Nonaka

(10) Patent No.: US 7,363,073 B2
(45) Date of Patent: Apr. 22, 2008

(54) METHOD AND APPARATUS FOR DISPLAYING VITAL SIGN DATA

(75) Inventor: Yukio Nonaka, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 564 days.

(21) Appl. No.: 10/242,456

(22) Filed: Sep. 13, 2002

(65) Prior Publication Data

US 2003/0055356 A1 Mar. 20, 2003

(30) Foreign Application Priority Data

Sep. 14, 2001 (JP) ............................ P2001-280229

(51) Int. Cl.
*A61B 5/04* (2006.01)
*A61B 5/02* (2006.01)
(52) U.S. Cl. ...................... 600/544; 600/483; 600/509; 600/500
(58) Field of Classification Search ................ 600/544, 600/545, 483, 481, 500–504, 508–526
See application file for complete search history.

(56) References Cited

U.S. PATENT DOCUMENTS 4,800,895 A 1/1989 Moberg et al.
6,052,619 A * 4/2000 John ........................... 600/544
6,224,549 B1 * 5/2001 Drongelen ................... 600/300

FOREIGN PATENT DOCUMENTS

DE 198 17 094 A1 10/1999

OTHER PUBLICATIONS

PEEG Monitor for-aimed control of anaesthesia.

* cited by examiner

*Primary Examiner*—Charles A. Marmor, II
*Assistant Examiner*—Navin Natnithithadha
(74) *Attorney, Agent, or Firm*—Sughrue Mion, PLLC

(57) ABSTRACT

An electroencephalogram waveform is displayed in a first display area in a real time manner such that a direction indicating lapse of time is oriented horizontally. A second display area is provided adjacent to the first display area in which CSA or DSA derived from the electroencephalogram waveform, which has been displayed in the first display area, is consecutively displayed. A pulse waveform is displayed in a third display area in a real time manner such that a direction indicating lapse of time is oriented horizontally. A fourth display area is provided adjacent to the third display area so that the pulse waveform, which has been displayed in the third display area, is consecutively displayed in a compressed form. The electroencephalogram waveform in the first display area and the pulse waveform in the third display area are displayed synchronously with each other. The CSA or the DSA in the second display area and the compressed pulse waveform in the fourth display area are displayed synchronously with each other.

26 Claims, 4 Drawing Sheets

METHOD AND APPARATUS FOR DISPLAYING VITAL SIGN DATA

BACKGROUND OF THE INVENTION

The invention relates to a method and an apparatus for displaying vital sign data, and more particularly, to a method and apparatus for displaying vital sign data, which monitor a vital sign signal of a patient in an intensive care unit (ICU), an operating room (OR), or a hospital ward in a medical facility.

An electroencephalograph or a like device measures analysis data (i.e., frequency spectra) of a patient consecutively in a medical facility and displays the thus-measured data in a predetermined arrangement. The electroencephalograph displays the data while arranging them vertically according to a display method called a compressed spectral array (CSA) display method or a density spectral array (DSA) display method.

As described in, e.g., U.S. Pat. No. 4,800,895, the CSA display method is for displaying a curve in which the horizontal axis represents a frequency and the vertical axis represents an amplitude of an electroencephalogram (EEG). Curves are displayed while being arranged in a vertical direction at given time intervals. The DSA display method is for providing a horizontal bar in which the horizontal axis represents a frequency and the brightness thereof at a portion corresponding to each frequency represents the amplitude of an EEG by density of dots (black dots). Horizontal bars are displayed while being arranged in a vertical direction at given time intervals.

In contrast, a bed-side monitor which displays other vital sign signals, such as an electrocardiogram (ECG) or a pulse wave, employs a display method of providing a display with the horizontal axis representing a time axis.

As mentioned, there has hitherto been employed a display method of displaying a vital sign signal other than an EEG with the horizontal axis representing a time axis. Further, there has hitherto been employed a display method of displaying EEG analysis data with the vertical axis representing a time axis.

However, when vital sign signals of a patient are monitored through use of a related-art electroencephalograph and a bed-side monitor, EEG analysis data are displayed with a time axis differing from that used for displaying another vial sign signal (e.g., an ECG or a pulse wave). Hence, difficulty is encountered in readily ascertaining a time relationship between the EEG analysis data and the other vital sign signal.

Therefore, in the event that the condition of a patient has changed, difficulty is encountered in analyzing and diagnosing a correlation between changes in an EEG and another vital sign signal and in specifying a cause of the changes in the patient's condition.

SUMMARY OF THE INVENTION

It is therefore an object of the present invention to provide a method and an apparatus for displaying vital sign data which enables immediate ascertainment of a time relationship between changes in another vital sign signal (e.g., an ECG or a pulse wave) and more accurate diagnosis of a cause of changes in a patient's condition, by displaying EEG analysis data and the vital sign signal on a single monitor screen with a single time axis.

In order to achieve the above object, according to the present invention, there is provided a vital sign displaying method, comprising the steps of:

providing a first display area in which an electroencephalogram waveform is displayed in a real time manner such that a direction indicating lapse of time is oriented horizontally;

providing a second display area adjacent to the first display area in which at least one of CSA and DSA derived from the electroencephalogram waveform, which has been displayed in the first display area, is consecutively displayed;

providing a third display area in which a pulse waveform is displayed in a real time manner such that a direction indicating lapse of time is oriented horizontally;

providing a fourth display area adjacent to the third display area in which the pulse waveform, which has been displayed in the third display area, is consecutively displayed in a compressed form;

displaying the electroencephalogram waveform in the first display area and the pulse waveform in the third display area synchronously with each other; and displaying at least one of the CSA and the DSA in the second display area and the compressed pulse waveform in the fourth display area synchronously with each other.

This method enables display of relevant data pertaining to an EEG and relevant data pertaining to a pulse wave with a single time axis, thereby enabling immediate ascertainment of a time relationship between changes in a vital sign signal. Hence, the method contributes to more accurate diagnosis of a cause of changes in a patient's condition.

According to the present invention, there is also provided a vital sign displaying method, comprising the steps of:

providing a first display area in which an electroencephalogram waveform is displayed in a real time manner such that a direction indicating lapse of time is oriented horizontally;

providing a second display area adjacent to the first display area in which at least one of CSA and DSA derived from the electroencephalogram waveform, which has been displayed in the first display area, is consecutively displayed;

providing a fifth display area in which an electrocardiogram waveform is displayed in a real time manner such that a direction indicating lapse of time is oriented horizontally;

providing a sixth display area adjacent to the fifth display area in which trend information derived from the electrocardiogram waveform, which has been displayed in the fifth display area, is consecutively displayed;

displaying the electroencephalogram waveform in the first display area and the electrocardiogram waveform in the fifth display area synchronously with each other; and displaying at least one of the CSA and the DSA in the second display area and the trend information in the sixth display area synchronously with each other.

This method enables display of relevant data pertaining to an EEG and relevant data pertaining to an ECG with a single time axis, thereby enabling immediate ascertainment of a time relationship between changes in a vital sign signal. Hence, the method enables contribution to more accurate diagnosis of a cause of changes in a patient's condition.

Preferably, the above methods further comprise the steps of:

applying a predetermined operation designating the second display area;

providing a new display area in accordance with the predetermined operation; and displaying at least one of the CSA and the DSA, which has been displayed in the second display area, in the new display area in an enlarged manner.

In this case, an enlarged DSA display and/or an enlarged CSA display can be provided in the thus-provided new displaying area. Hence, more detailed ascertainment of an EEG waveform can be attained.

According to the present invention, there is also provided a vital sign displaying apparatus, comprising:

an electroencephalogram electrode, which detects an electroencephalogram waveform of a patient;

a pulse wave sensor, which detects a pulse waveform of the patient;

first display means, for providing a first display area in which the electroencephalogram waveform is displayed in a real time manner such that a direction indicating lapse of time is oriented horizontally;

second display means, for providing a second display area adjacent to the first display area in which at least one of CSA and DSA derived from the electroencephalogram waveform, which has been displayed in the first display area, is consecutively displayed;

third display means, for providing a third display area in which the pulse waveform is displayed in a real time manner such that a direction indicating lapse of time is oriented horizontally; and fourth display means, for providing a fourth display area adjacent to the third display area in which the pulse waveform, which has been displayed in the third display area, is consecutively displayed in a compressed form, wherein:

the electroencephalogram waveform in the first display area and the pulse waveform in the third display area are displayed synchronously with each other; and at least one of the CSA and the DSA in the second display area and the compressed pulse waveform in the fourth display area are displayed synchronously with each other.

In this case, relevant data pertaining to an EEG and relevant data pertaining to a pulse wave are displayed with a single time axis, thereby enabling immediate ascertainment of a time relationship between changes in a vital sign signal. Hence, the method enables contribution to more accurate diagnosis of a cause of changes in a patient's condition.

According to the present invention, there is also provided a vital sign displaying apparatus, comprising:

an electroencephalogram electrode, which detects an electroencephalogram waveform of a patient;

a pulse wave sensor, which detects a pulse waveform of the patient;

first display means, for providing a first display area in which the electroencephalogram waveform is displayed in a real time manner such that a direction indicating lapse of time is oriented horizontally;

second display means, for providing a second display area adjacent to the first display area in which at least one of CSA and DSA derived from the electroencephalogram waveform, which has been displayed in the first display area, is consecutively displayed;

fifth display means, for providing a fifth display area in which an electrocardiogram waveform is displayed in a real time manner such that a direction indicating lapse of time is oriented horizontally; and sixth display means, for providing a sixth display area adjacent to the fifth display area in which trend information derived from the electrocardiogram waveform, which has been displayed in the fifth display area, is consecutively displayed, wherein:

the electroencephalogram waveform in the first display area and the electrocardiogram waveform in the fifth display area are displayed synchronously with each other; and at least one of the CSA and the DSA in the second display area and the trend information in the sixth display area are displayed synchronously with each other.

In this case, the DSA or the CSA and the trend information are displayed with a single time axis, thereby enabling immediate ascertainment of a time relationship between changes in a vital sign signal. Hence, the method enables contribution to more accurate diagnosis of a cause of changes in a patient's condition.

Preferably, the vital sign displaying apparatus further comprises:

means for detecting that a predetermined operation designating the second display area is applied; and means for providing a new display area when the predetermined operation is detected, the new display area displaying at least one of the CSA and the DSA, which has been displayed in the second display area, in an enlarged manner.

In this case, an enlarged DSA or CSA display is displayed in the new display area, thereby enabling more detailed ascertainment of an EEG waveform.

According to the present invention, there is also provided a vital sign displaying method, comprising the steps of:

providing a first display area in which an electroencephalogram waveform is displayed in a real time manner such that a direction indicating lapse of time is oriented horizontally;

providing a second display area adjacent to the first display area in which at least one of CSA and DSA derived from the electroencephalogram waveform, which has been displayed in the first display area, is consecutively displayed;

providing a third display area in which a vital sign waveform other than the electroencephalogram waveform is displayed in a real time manner such that a direction indicating lapse of time is oriented horizontally;

providing a fourth display area adjacent to the third display area in which the vital sign waveform, which has been displayed in the third display area, is consecutively displayed in a compressed form; and displaying at least one of the CSA and the DSA in the second display area and the compressed vital sign waveform in the fourth display area synchronously with each other.

This method enables display of relevant data pertaining to an EEG and relevant data pertaining to another vital sign signal with a single time axis, thereby enabling immediate ascertainment of a time relationship between changes in a vital sign signal. Hence, the method enables contribution to more accurate diagnosis of a cause of changes in a patient's condition.

Preferably, the method further comprises the step of displaying the electroencephalogram waveform in the first display area and the vital sign waveform in the third display area synchronously with each other.

Preferably, the method further comprises the steps of:

applying a predetermined operation designating the second display area;

providing a new display area in accordance with the predetermined operation; and displaying at least one of the CSA and the DSA, which has been displayed in the second display area, in the new display area in an enlarged manner.

According to the present invention, there is also provided a vital sign displaying apparatus, comprising:

an electroencephalogram electrode, which detects an electroencephalogram waveform of a patient;

first display means, for providing a first display area in which the electroencephalogram waveform is displayed in a real time manner such that a direction indicating lapse of time is oriented horizontally; and second display means, for providing a second display area adjacent to the first display area in which at least one of CSA and DSA derived from the electroencephalogram waveform, which has been displayed in the first display area, is consecutively displayed.

Preferably, the vital sign displaying apparatus further comprises:

means for detecting that a predetermined operation designating the second display area is applied; and means for providing a new display area when the predetermined operation is detected, the new display area displaying at least one of the CSA and the DSA, which has been displayed in the second display area, in an enlarged manner.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE PREFERRED EMBODIMENTS

An embodiment of a method and apparatus for displaying vital sign data according to the invention will be described in detail hereinbelow by reference to the accompanying drawings.

Figure 1:
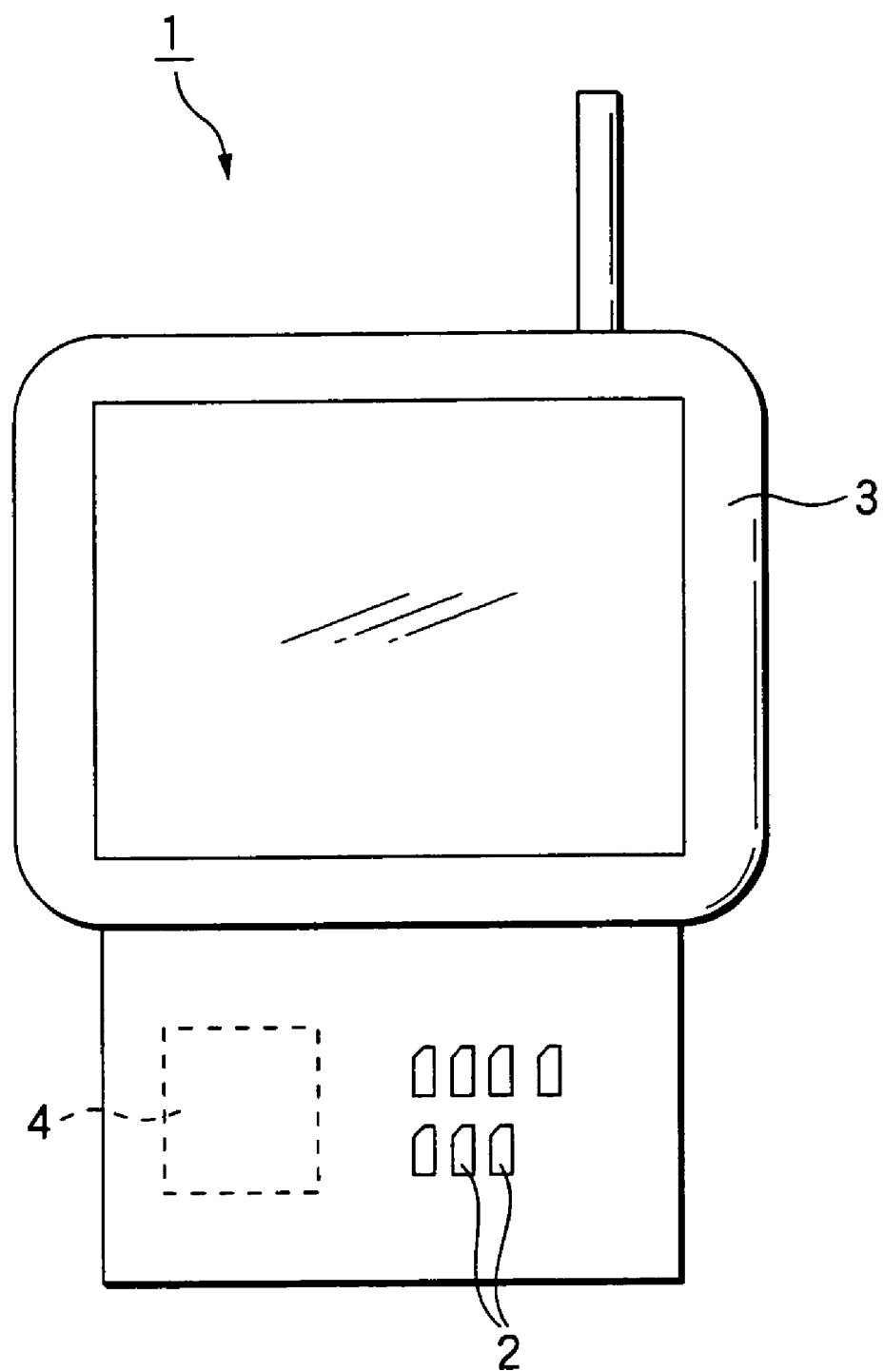
FIG. 1 is an illustration showing an external view of a vital sign displaying apparatus according to an embodiment of the present invention.

FIG. 1 is an illustration showing an external view of a vital sign displaying apparatus according to an embodiment.

As shown in FIG. 1, a vital sign displaying apparatus 1 of the embodiment (e.g., a bedside monitor) has a cable connection terminal 2, a display screen 3, and a data processor 4.

Vital sign data, such as a pulse wave or an ECG, are detected by sensors or electrodes attached to a patient. The thus-detected vital sign data can be input to the vital sign displaying apparatus 1 by connecting signal cables extending from sensors or like elements with the cable connection terminal 2. A built-in amplifier or an external amplifier may be employed. Relevant data pertaining to an EEG (hereinafter referred to as "EEG relevant data") may also be input to the vital sign displaying apparatus 1 through use of an electrode for EEG and an electroencephalograph.

Here, various types of vital sign data (e.g., a pulse wave, an ECG, and an EEG) may be input to the vital sign displaying apparatus 1 by wireless connection.

The various vital sign data (e.g., a pulse wave, an ECG, and an EEG) that have been entered in the manner as mentioned above are subjected to data processing to be performed by the data processor 4, such as a CPU. The thus-processed data are displayed on the display screen 3. Here, rather than being provided in a chassis of the vital sign displaying apparatus 1, the data processor 4 may be provided separately.

The data processor 4 comprises means for displaying relevant data pertaining to an EEG (hereinafter called "EEG data display means"); means for displaying relevant data pertaining to a pulse wave (hereinafter called "pulse wave data display means"); means for displaying relevant data pertaining to an ECG (hereinafter called "ECG data display means"); first screen display means; second screen display means; third screen display means; fourth screen display means; fifth screen display means; sixth screen display means; and enlarged screen display means. These means display various types of vital sign data on the display screen 3, the screen being separated into a plurality of display areas, in the form of a waveform display, a compressed waveform display, a trend display, a CSA (compressed spectral array) display, and a DSA (density spectral array) display.

The display method using these screen display means will now be described in detail.

Figure 2:
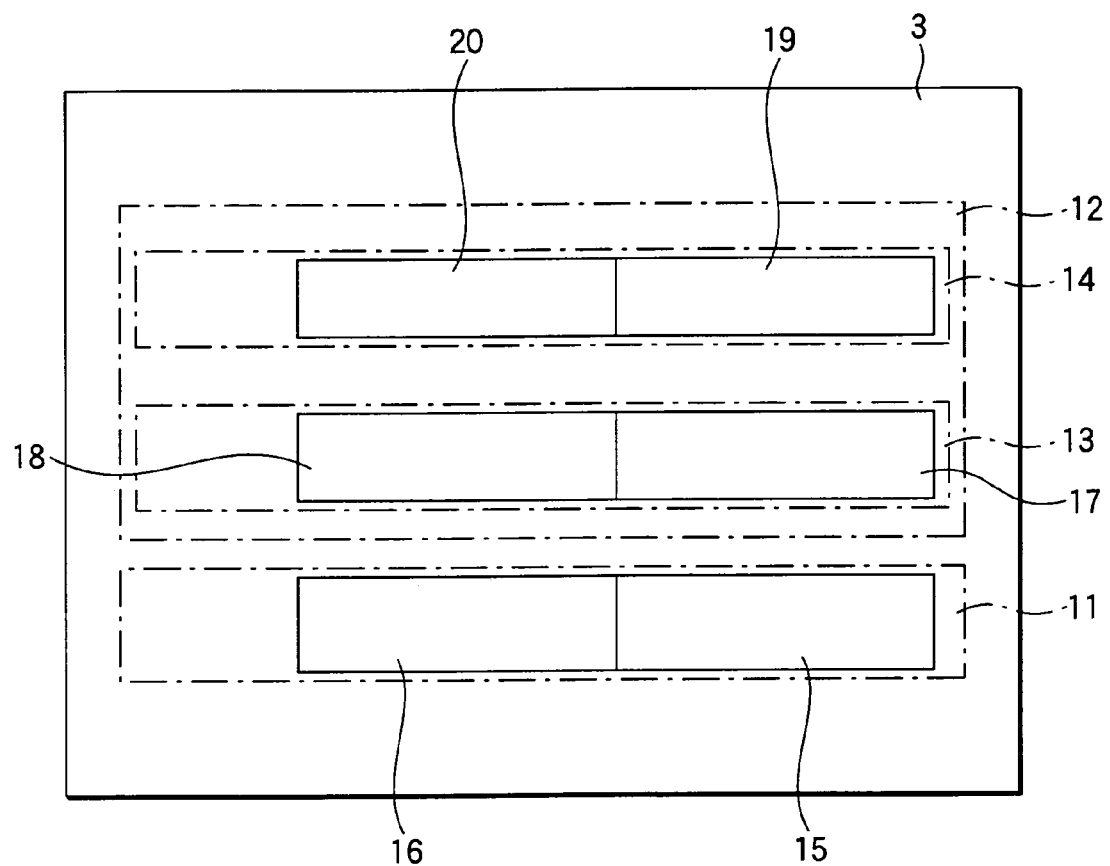
FIG. 2 is a view showing segments of a display area on a display screen of the vital sign displaying apparatus.

FIG. 2 shows segments of a display area of the vital sign displaying apparatus of the embodiment.

As shown in FIG. 2, according to the vital sign displaying method of the embodiment, the display screen 3 is separated into a plurality of display areas and has a vital sign data display area 12. The vital sign data display area 12 comprises a screen area 11 for displaying relevant data pertaining to an EEG (hereinafter called an "EEG data display area"); a screen area 13 for displaying relevant data pertaining to a pulse wave (hereinafter called a "pulse wave data display area"); and a screen area 14 for displaying relevant data pertaining to an ECG (hereinafter called an "ECG data display area").

The EEG data display area 11 has a first screen area 15 and a second screen area 16. An EEG waveform is displayed in the first screen area 15 in a real time manner with lapse of time in a horizontal direction. The second screen area 16 is provided so as to adjoin consecutively the side of the first screen area 15 with lapse of time in a horizontal direction. The CSA or the DSA derived from the EEG waveform, which has been displayed in the first screen area 15 in a real time manner, is consecutively displayed in the second screen area 16.

Vital sign data other than the EEG relevant data is displayed in the vital sign data display area 12. Further, the pulse wave data display area 13 included in the vital sign data display area 12 has a third screen area 17 and a fourth screen area 18. A pulse waveform is displayed in the third screen area 17 in a real time manner with lapse of time in a horizontal direction, and in synchronism with lapse of time in the EEG data display area 11. The fourth screen area 18 is provided so as to adjoin consecutively the side of the third screen area 17 with lapse of time in a horizontal direction. The pulse waveform displayed in the third screen area 17 in a real time manner is displayed in the fourth screen area 18, in the form of a compressed display.

Further, the ECG data display area 14 included in the vital sign data display area 12 has a fifth screen area 19 and a sixth screen area 20. An ECG waveform is displayed in the fifth screen area 19 in a real time manner in synchronism with elapse of a time in the EEG data display area 11 with lapse of time in a horizontal direction. The sixth screen area 20 is provided so as to adjoin consecutively the side of the fifth screen area 19 with lapse of time in a horizontal direction. A heart rate (ECG waveform relevant data), which is to be determined from an ECG waveform displayed in the fifth screen area 19 in a real time manner, is consecutively displayed in the sixth screen area 20 in the form of a trend display.

Vital sign data other than the pulse wave relevant data and the ECG relevant data can also be displayed in the vital sign data display area 12.

A boundary separating the second screen area 16 from the first screen area 15, a boundary separating the fourth screen area 18 from the third screen area 17, and a boundary separating the sixth screen area 20 from the fifth screen area 19 are aligned into a single vertical line on the screen. By a screen operation, the boundaries may be shifted laterally in parallel with the single vertical line while remaining aligned in a line.

A DSA display or a CSA display derived from the EEG waveform in the second screen area 16, a compressed display of a pulse waveform in the fourth screen area 18, and a trend display of a heart rate in the sixth screen area 20 are displayed synchronously.

The CSA display of the embodiment has the vertical axis representing the frequency of an EEG spectrum and the horizontal axis representing a frequency spectrum. CSA displays are provided horizontally at given time intervals. The frequency spectrum may be a power spectrum or a voltage spectrum.

The DSA display of the embodiment is provided in the form of dark and bright patterns in accordance with the intensity of frequency spectrum of an EEG, with the vertical axis representing a frequency and the horizontal axis representing time. Dark and bright patterns may be formed by controlling density of dots (black dots). Alternatively, dark and bright patterns may be displayed by a change in color, such as monochrome gradation or gradations in color.

Rather than being displayed in the sequence shown in FIG. 2, display areas of the previously-described vital sign data (i.e., a pulse wave, an ECG, and an EEG) may be displayed in an arbitrary (vertical) sequence.

An example of the display screen 3 of the vital sign displaying apparatus of the embodiment on which various vital sign data are actually displayed will be described by reference to FIG. 3.

As shown in this figure, HR (heart rate) and ST (ECG S-T segment) are displayed on the display screen 3 as ECG waveform relevant data (in an area corresponding to the ECG data display area 14 shown in FIG. 2). Moreover, ART (arterial blood pressure), PAP (pulmonary arterial pressure), and CVP (central venous pressure) are displayed as pulse wave relevant data (in an area corresponding to the pulse wave data display area 13 shown in FIG. 2). Further, a waveform of ICP (intra cranial pressure) and a waveform of $CO_2$ (carbon dioxide partial pressure) are displayed.

A waveform of an EEG1 (an EEG of first channel) and a waveform of EEG2 (an EEG of second channel) are displayed as EEG relevant data (in an area corresponding to the EEG data display area 11 shown in FIG. 2).

A current numerical value (e.g., a current HR of 80) is displayed in the left-side area on the screen for each vital sign data waveform. Numerals provided in the right-side area on the screen show scales of the vertical axis for the respective waveforms.

Portions of the respective waveforms on the right side of a virtual screen partition P located in substantially the center of the display are displayed in a real time manner and in sequence of lapse of time so as to go back in time from the right end (current time) toward the left side (areas corresponding to the first screen area 15, the third screen area 17, and the fifth screen area 19 shown in FIG. 2).

Portions of the respective waveforms on the left side of the virtual screen partition P are displayed with a compressed time scale. HR is provided in the form of a trend display (in an area corresponding to the sixth screen area 20 shown in FIG. 2). ART, PAP, and CVP are provided in the form of a compressed display (in an area corresponding to the fourth screen area 18 shown in FIG. 2). EEG 1 and EEG 2 are provided in the form of a DSA display (in an area corresponding to the second screen area 16 shown in FIG. 2).

Figure 3:
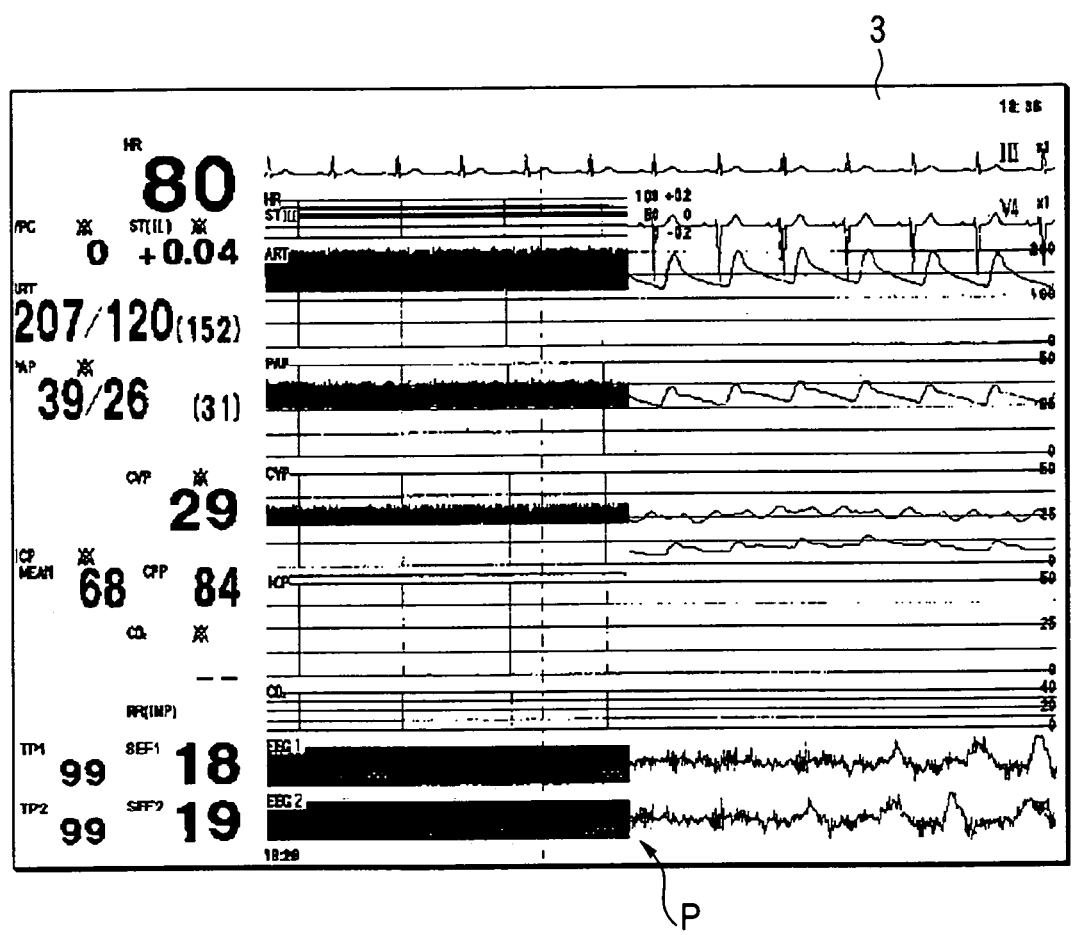
FIG. 3 is an illustration showing a display example in which various types of vital sign data are displayed in a display screen of the vital sign displaying apparatus.

As shown in FIG. 3, only the ECG waveform on the top row is displayed in a real time manner, without regard to the screen partition.

A plurality of windows may be opened in the display screen 3 so that various types of data can be displayed in the respective windows.

Figure 4:
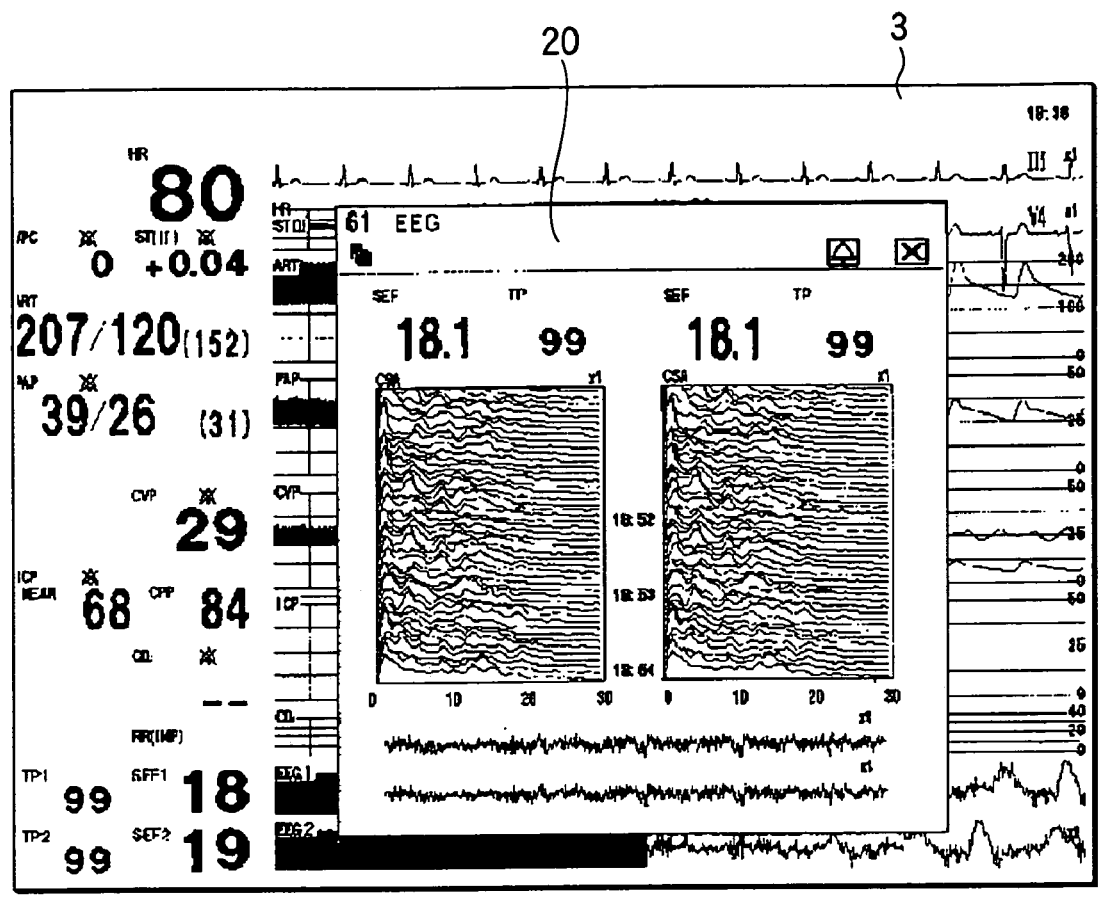
FIG. 4 is an illustration showing a case where a CSA display is enlargedly provided in another window in the display example shown in FIG. 3.

For example, FIG. 4 shows a case where another window is opened in a display example shown in FIG. 3 and an enlarged CSA display is provided in the thus-opened window.

As shown in FIG. 4, another window 20 is opened by clicking a cursor within the area on the display screen 3 in which EEG relevant data are provided in the form of the DSA display (corresponding to the second screen area 16 shown in FIG. 2). A CSA display of data pertaining to the EEG 1 and a CSA display of data pertaining to the EEG 2, both data available for a time period in the vicinity of a time point at which the cursor is clicked, are displayed in the thus-opened window in a vertically-enlarged form. In the case of the display example shown in FIG. 4, EEG waveforms of respective channels are displayed in a lower portion of the window.

The window can provide an enlarged DSA display in place of the CSA display. Further, both an enlarged CSA display and an enlarged DSA display may be provided. The enlarged CSA display and the enlarged DSA display may also be provided horizontally.

In a case where a DSA display in the second screen area is provided by changes in color, such as gradations in color, the enlarged CSA display may be colored in accordance with the color of the DSA display when the DSA display is provided in the form of an enlarged CSA display in another window.

In the above embodiment, it is explained a case where the first screen area, the third screen area and the fifth screen area are synchronously displayed in a real time manner. However, they are not necessary to be displayed synchronously when the signal-passing speeds in the respective screen areas are not identical with each other.

Although the present invention has been shown and described with reference to specific preferred embodiments, various changes and modifications will be apparent to those skilled in the art from the teachings herein. Such changes and modifications as are obvious are deemed to come within the spirit, scope and contemplation of the invention as defined in the appended claims.

For example, in the above embodiments, although either the CSA or the DSA is displayed in the second screen area, both of the CSA and DSA may be displayed in the second screen area as required.

What is claimed is:

1. A vital sign displaying method, comprising the steps of:
providing a first display area in which an electroencephalogram waveform is displayed in a real time manner such that a direction indicating lapse of time is oriented horizontally;
providing a second display area adjacent to the first display area in which at least one of CSA and DSA derived from the electroencephalogram waveform, which has been displayed in the first display area, is consecutively displayed such that a direction indicating lapse of time is oriented horizontally;
providing a third display area in which a pulse waveform is displayed in a real time manner such that a direction indicating lapse of time is oriented horizontally;
providing a fourth display area adjacent to the third display area in which the pulse waveform, which has been displayed in the third display area, is consecutively displayed in a compressed form;
displaying the electroencephalogram waveform in the first display area and the pulse waveform in the third display area in such a manner that data points representing the same time in the electroencephalogram waveform and the pulse waveform are aligned vertically; and
displaying at least one of the CSA and the DSA in the second display area and the compressed pulse waveform in the fourth display area in such a manner that points representing the same time in the at least one of the CSA and the DSA, and the compressed pulse waveform, are aligned vertically.

2. The vital sign displaying method as set forth in claim 1, further comprising the steps of:
applying a predetermined operation designating the second display area;
providing a new display area in accordance with the predetermined operation; and
displaying at least one of the CSA and the DSA, which has been displayed in the second display area, in the new display area in an enlarged manner.

3. The vital sign displaying method as set forth in claim 1, wherein the first display area is disposed laterally adjacent to and horizontally aligned with the second display area, and
wherein the third display area is disposed laterally adjacent to and horizontally aligned with the fourth display area.

4. The vital sign displaying method as set forth in claim 3, wherein the first display area is vertically aligned with the third display area, and
wherein the second display area is vertically aligned with the fourth display area.

5. The vital sign displaying method as set forth in claim 1, wherein:
a horizontal width in the first display area corresponding to a first time period and a horizontal width in the third display area corresponding to the first time period are identical; and
a horizontal width in the second display area corresponding to a second time period and a horizontal width in the fourth display area corresponding to the second time period are identical.

6. A vital sign displaying method, comprising the steps of:
providing a first display area in which an electroencephalogram waveform is displayed in a real time manner such that a direction indicating lapse of time is oriented horizontally;
providing a second display area adjacent to the first display area in which at least one of CSA and DSA derived from the electroencephalogram waveform, which has been displayed in the first display area, is consecutively displayed such that a direction indicating lapse of time is oriented horizontally;
providing a third display area in which an electrocardiogram waveform is displayed in a real time manner such that a direction indicating lapse of time is oriented horizontally;
providing a fourth display area adjacent to the third display area in which trend information derived from the electrocardiogram waveform, which has been displayed in the third display area, is consecutively displayed;
displaying the electroencephalogram waveform in the first display area and the electrocardiogram waveform in the third display area in such a manner that data points representing the same time in the electroencephalogram waveform and the electrocardiogram waveform are aligned vertically; and
displaying at least one of the CSA and the DSA in the second display area and the trend information in the fourth display area in such a manner that points representing the same time in the at least one of the CSA and the DSA, and the trend information, are aligned vertically.

7. The vital sign displaying method as set forth in claim 6, further comprising the steps of:
applying a predetermined operation designating the second display area;
providing a new display area in accordance with the predetermined operation; and
displaying at least one of the CSA and the DSA, which has been displayed in the second display area, in the new display area in an enlarged manner.

8. The vital sign displaying method as set forth in claim 6, wherein the first display area is disposed laterally adjacent to and horizontally aligned with the second display area, and
wherein the third display area is disposed laterally adjacent to and horizontally aligned with the fourth display area.

9. The vital sign displaying method as set forth in claim 8, wherein the first display area is vertically aligned with the third display area, and
wherein the second display area is vertically aligned with the fourth display area.

10. The vital sign displaying method as set forth in claim 6, wherein:
a horizontal width in the first display area corresponding to a first time period and a horizontal width in the third display area corresponding to the first time period are identical; and
a horizontal width in the second display area corresponding to a second time period and a horizontal width in the fourth display area corresponding to the second time period are identical.

11. A vital sign displaying apparatus, comprising: an electroencephalogram electrode, which detects an electroencephalogram waveform of a patient;
a pulse wave sensor, which detects a pulse waveform of the patient;
means for providing a first display area in which the electroencephalogram waveform is displayed in a real time manner such that a direction indicating lapse of time is oriented horizontally;

means for providing a second display area adjacent to the first display area in which at least one of CSA and DSA derived from the electroencephalogram waveform, which has been displayed in the first display area, is consecutively displayed such that a direction indicating lapse of time is oriented horizontally;

means for providing a third display area in which the pulse waveform is displayed in a real time manner such that a direction indicating lapse of time is oriented horizontally; and means for providing a fourth display area adjacent to the third display area in which the pulse waveform, which has been displayed in the third display area, is consecutively displayed in a compressed form, wherein:

the electroencephalogram waveform in the first display area and the pulse waveform in the third display area are displayed in such a manner that data points representing the same time in the electroencephalogram waveform and the pulse waveform are aligned vertically; and at least one of the CSA and the DSA in the second display area and the compressed pulse waveform in the fourth display area are displayed in such a manner that points representing the same time in the at least one of the CSA and the DSA, and the compressed pulse waveform, are aligned vertically.

12. The vital sign displaying apparatus as set forth in claim 11 further comprising:

means for detecting that a predetermined operation designating the second display area is applied; and means for providing a new display area when the predetermined operation is detected, the new display area displaying at least one of the CSA and the DSA, which has been displayed in the second display area, in an enlarged manner.

13. The vital sign displaying apparatus as set forth in claim 11, wherein the first display area is disposed laterally adjacent to and horizontally aligned with the second display area, and wherein the third display area is disposed laterally adjacent to and horizontally aligned with the fourth display area.

14. The vital sign displaying apparatus as set forth in claim 13, wherein the first display area is vertically aligned with the third display area, and wherein the second display area is vertically aligned with the fourth display area.

15. The vital sign displaying apparatus as set forth in claim 11, wherein:

a horizontal width in the first display area corresponding to a first time period and a horizontal width in the third display area corresponding to the first time period are identical; and a horizontal width in the second display area corresponding to a second time period and a horizontal width in the fourth display area corresponding to the second time period are identical.

16. A vital sign displaying apparatus, comprising:

an electroencephalogram electrode, which detects an electroencephalogram waveform of a patient;

an electrocardiogram wave sensor, which detects an electrocardiogram waveform of the patient;

means for providing a first display area in which the electroencephalogram waveform is displayed in a real time manner such that a direction indicating lapse of time is oriented horizontally;

means for providing a second display area adjacent to the first display area in which at least one of CSA and DSA derived from the electroencephalogram waveform, which has been displayed in the first display area, is consecutively displayed such that a direction indicating lapse of time is oriented horizontally;

means for providing a third display area in which the electrocardiogram waveform is displayed in a real time manner such that a direction indicating lapse of time is oriented horizontally; and means for providing a fourth display area adjacent to the third display area in which trend information derived from the electrocardiogram waveform, which has been displayed in the display area, is consecutively displayed, wherein:

the electroencephalogram waveform in the first display area and the electrocardiogram waveform in the third display area are displayed in such a manner that data points representing the same time in the electroencephalogram waveform and the electrocardiogram waveform are aligned vertically; and at least one of the CSA and the DSA in the second display area and the trend information in the fourth display area are displayed in such a manner that points representing the same time in the at least one of the CSA and the DSA, and the trend information, are aligned vertically.

17. The vital sign displaying apparatus as set forth in claim 16, further comprising:

means for detecting that a predetermined operation designating the second display area is applied; and means for providing a new display area when the predetermined operation is detected, the new display area displaying at least one of the CSA and the DSA, which has been displayed in the second display area, in an enlarged manner.

18. The vital sign displaying apparatus as set forth in claim 16, wherein the first display area is disposed laterally adjacent to and horizontally aligned with the second display area, and wherein the third display area is disposed laterally adjacent to and horizontally aligned with the fourth display area.

19. The vital sign displaying apparatus as set forth in claim 18, wherein the first display area is vertically aligned with the third display area, and wherein the second display area is vertically aligned with the fourth display area.

20. The vital sign displaying apparatus as set forth in claim 16, wherein:

a horizontal width in the first display area corresponding to a first time period and a horizontal width in the third display area corresponding to the first time period are identical; and a horizontal width in the second display area corresponding to a second time period and a horizontal width in the fourth display area corresponding to the second time period are identical.

21. A vital sign displaying method, comprising the steps of:

providing a first display area in which an electroencephalogram waveform is displayed in a real time manner such that a direction indicating lapse of time is oriented horizontally;

providing a second display area adjacent to the first display area in which at least one of CSA and DSA derived from the electroencephalogram waveform, which has been displayed in the first display area, is consecutively displayed such that a direction indicating lapse of time is oriented horizontally;

providing a third display area in which a vital sign waveform other than the electroencephalogram waveform is displayed in a real time manner such that a direction indicating lapse of time is oriented horizontally;

providing a fourth display area adjacent to the third display area in which the vital sign waveform, which has been displayed in the third display area, is consecutively displayed in a compressed form; and displaying at least one of the CSA and the DSA in the second display area and the compressed vital sign waveform in the fourth display area in such a manner that points representing the same time in the at least one of the CSA and the DSA, and the compressed vital sign waveform, are aligned vertically.

22. The vital sign displaying method as set forth in claim 21, further comprising the step of displaying the electroencephalogram waveform in the first display area and the vital sign waveform in the third display area synchronously with each other.

23. The vital sign displaying method as set forth in claim 21, further comprising the steps of:

applying a predetermined operation designating the second display area;

providing a new display area in accordance with the predetermined operation; and displaying at least one of the CSA and the DSA, which has been displayed in the second display area, in the new display area in an enlarged manner.

24. The vital sign displaying method as set forth in claim 21, wherein the first display area is disposed laterally adjacent to and horizontally aligned with the second display area, and wherein the third display area is disposed laterally adjacent to and horizontally aligned with the fourth display area.

25. The vital sign displaying method as set forth in claim 24, wherein the first display area is vertically aligned with the third display area, and wherein the second display area is vertically aligned with the fourth display area.

26. The vital sign displaying method as set forth in claim 21, wherein:

a horizontal width in the first display area corresponding to a first time period and a horizontal width in the third display area corresponding to the first time period are identical; and a horizontal width in the second display area corresponding to a second time period and a horizontal width in the fourth display area corresponding to the second time period are identical.

* * * * *